United States Patent [19]
Suzuki et al.

[11] Patent Number: 4,783,408
[45] Date of Patent: Nov. 8, 1988

[54] METHOD FOR THE PREPARATION OF A FUNGAL BODY AND A LIPID RICH IN γ-LINOLENIC ACID THEREFROM

[75] Inventors: Osamu Suzuki, Tsuchiura; Toshihiro Yokochi, Sakura, both of Japan

[73] Assignee: Director-General of the Agency of Industrial Science & Technology, Tokyo, Japan

[21] Appl. No.: 929,601

[22] Filed: Nov. 10, 1986

Related U.S. Application Data

[63] Continuation of Ser. No. 653,063, Sep. 21, 1984.

[30] Foreign Application Priority Data

Feb. 9, 1984 [JP] Japan .................................. 59-22394
Jun. 5, 1984 [JP] Japan ................................. 59-115162

[51] Int. Cl.$^4$ .............................................. C12P 7/64
[52] U.S. Cl. .................................... 435/134; 435/135; 435/244; 435/911; 435/254
[58] Field of Search ............... 435/135, 136, 244, 245, 435/911, 254

[56] References Cited

PUBLICATIONS

Journal of General Microbiology, (1965), 41, 127–134, Nutritional Factors in Relation to Growth and Fat Synthesis in Mortierella Vinacea, Chesters C.G.C.
Chem. Abs., vol. 98, p. 537, #33069f, Lipid High in —Linolenic Acid.

Primary Examiner—Charles F. Warren
Assistant Examiner—Irene Marx
Attorney, Agent, or Firm—Wyatt, Gerber, Burke and Badie

[57] ABSTRACT

A very efficient microbiological method is proposed for the preparation of γ-linolenic acid or a lipid rich in the content of γ-linolenic acid, one of the essential fatty acids in the diet of mammals, e.g. human. The method comprises culturing a fungus of Mortierella genus including *isabellina, vinacea, ramanniana, ramanniana* var. *angulispora* and *nana* in a culture medium containing a carbohydrate, e.g. glucose, as the carbon source in an unusually high concentration of 60 to 400 g/liter to grow a fungal body containing a large amount of a lipid rich in the content of γ-linolenic acid. A further improvement in the efficiency of culture and the content of the desired fatty acid in the fungal body is obtained by the addition of acetic acid or an alkali acetate to the culture medium.

5 Claims, No Drawings

METHOD FOR THE PREPARATION OF A FUNGAL BODY AND A LIPID RICH IN γ-LINOLENIC ACID THEREFROM

BACKGROUND OF THE INVENTION

The present invention relates to a method for the preparation of a fungal body and a lipid rich in γ-linolenic acid therefrom. More particularly, the invention relates to a method for the preparation of a fungal body of certain filamentous fungi belonging to the genus of Mortierella containing a large amount of lipids by cultivation under specific conditions and a lipid therefrom which is rich in the content of γ-linolenic acid.

It has been hitherto reported that several fungal bodies contain a considerably large amount of lipids including neutral lipids, i.e. oils and fats, and polar lipids, i.e. phospholipids and glycolipids, in a content of, for example, 25 to 65% by weight on the dry basis. Such high-lipid filamentous fungus moulds are exemplified by *Geotricum candidum, Fusarium lini, Fusarium buligenum, Penicillium lilacinum, Penicillium soppi, Penicillium spinulosum, Aspergillus nidulance* and *Mucor sacineleudes* reported by K. Yamada [Food-Industrial Microbiology, page 63], *Mortierella vinacea* reported by C. G. C. Chester et al. [J. Gen. Microbiol., volume 41 (1965), page 127] and *Aspergillus terreus, Aspergillus ochraceus, Cladosporium fulvum, Cladosporium herbarum* and *Penicillium gladioli* reported by J. Singh et al. [J. Sci. Fd. Agric., volume 23 (1972), page 1113].

These fungi can be cultured in a culture medium containing a carbohydrate as the carbon source and the preferable concentration of the carbohydrate as the nutrient in the culture medium is reportedly 20 to 60 g/liter when they are cultured in a flask or in a small-size culture tank. When a fungal body of high lipid content is desired of these fungi, the velocity and extent of the multiplication of the filamentous fungal body are usually not so high that the carbohydrate as the carbon source is not exhaustively consumed. For example, it is reported by C. G. C. Chester et al. that the best results obtained in the culture of *Mortierella vinacea* were that the use of a culture medium containing glucose in an initial concentration of 21.2 g/liter at 20° C. gave 4.7 g/liter of the fungal body as dried containing 3 g/liter of the lipid extractabale therefrom after consumption of 17 g/liter of starting glucose for 10 days. When molasses is used as the carbon source in the culture of *Penicillium spinurosum*, it is noted that the increase in the concentration of the carbon source in the culture medium does not contribute to the increase of the multiplication of the fungal body so much with rather decreased proportion of the consumed carbon source on the contrary. In this case, the highest results reported by A. W. Khen et al. [Can. J. Microbiol., volume 7 (1961), page 895] are that the amount of the fungal body multiplication as dried was 22 g/liter corresponding to only 2.5 g/liter of the lipid extractable therefrom after 6 days of culture at 30° C. starting with a molasses concentration of 164 g/liter of which about 40% is consumed by the multiplication of the fungus.

Turning now to the nature or constituents of the lipids derived from such a fungal body, a recent concern in the pharmaceutical industry is the preparation of γ-linolenic acid from the lipids. As is well known, γ-linolenic acid, i.e. cis-6,9,12-octadecatrienoic acid which cannot be synthesized in the living body, is one of the essential fatty acids indispensable in the diet for mammals including human. This is because γ-linolenic acid taken into a living body is a precursor of and converted into bis-homo-γ-linolenic acid and further into arachidonic acid which in turn are converted into prostaglandins $E_1$ and $F_{1\alpha}$ and prostaglandins $E_2$ and $F_{2\alpha}$, respectively, playing very important roles in the living body so that deficiency of γ-linolenic acid in the diet causes various diseases and disorder of the body requiring administration thereof in the form of a medicine.

γ-Linolenic acid or a lipid containing the same is conventionally obtained by extracting from the seeds of several plants such as evening primrose (*Oenothera biennis* L.) but the productivity thereof is quite unsatisfactory. Therefore, great efforts are continuously directed, for example, by R. B. Wolt et al. to seek a plant giving seeds containing an oil rich in the content of γ-linolenic acid [J. Amer. Oil Chem. Soc., volume 60 (1983), page 1858]. Unfortunately, all of the plants reportedly producing a lipid containing a promising amount of γ-linolenic acid are rare with low availability so that collection of a large amount of the seeds thereof is a rather difficult matter with no possibility of industrial production of γ-linolenic acid with high productivity.

An alternative possibility for the industrial preparation of γ-linolenic acid or a lipid rich in the content thereof would be given by a microbiological method when and if a microorganism efficiently producing such a lipid is discovered and an industrially efficient method for the cultivation of such a microorganism is established since the microbiological production can be performed usually without supply of the sunlight energy so that the productivity is never affected by the weather. Any large facilities for the industrial production of γ-linolenic acid can be constructed on a relatively small land area in comparison with the agricultural fields necessary for the growth of the specific plant and the rate of production can freely be controlled according to desire.

Several microorganisms are known to produce lipids containing a relatively large amount of γ-linolenic acid including *Mucor globosus* and *Mucor pusillus* reported by R. O. Mumma et al. [Lipids, volume 6 (1971), page 584], *Choanephora cucurbitarum* reported by H. B. White, Jr. et al. [Biochim. Biophys. Acta, volume 116 (1966), page 388], *Pythium debaryanum, Saprolegnia litoralis, Rhizopus stolonifer, Rhizopus arrhizus, Phycomyces blakesleeanus, Mucor javanicus* and *Helicostylum pyriforme* reported by R. Shaw [Biochim. Biophys. Acta, volume 98 (1965), page 230] and *Entomophtora coronata* reported by R. O. Mumma et al. [Lipids, volume 5 (1970), page 915].

Each of the research works reported by the above named authors, however, is only experimental using a glass flask or a small culture tank and the starting concentration of the carbohydrate as the carbon source in the culture medium is limited to 20 to 60 g/liter. The amount of the fungal body obtained by the culture per unit volume of the medium is relatively small and the content of lipids in the fungal body is only 3 to 30% by weight so that the microbiological way so far developed is also not quite promising as an industrial method for the production of γ-linolenic acid or a lipid rich in the content thereof insofar as the above named microorganisms are utilized as the objective of the culture.

SUMMARY OF THE INVENTION

A primary object of the present invention is to provide a microbiological method for the production of a lipid rich in the content of γ-linolenic acid or preparation of γ-linolenic acid therefrom.

Another object of the invention is to provide a method for the preparation of a fungal body containing a lipid rich in the content of γ-linolenic acid by the culture in a liquid culture medium with a markedly increased efficiency.

Thus, the method of the invention for the preparation of a fungal body containing a large amount of a lipid rich in the content of γ-linolenic acid comprises culturing a fungal stock selected from the group consisting of *Mortierella isabellina*, *Mortierella vinacea*, *Mortierella ramanniana*, *Mortierella ramanniana* var. *angulispora* and *Mortierella nana* under aeration in a liquid culture medium containing a carbohydrate as the carbon source at a concentration in the range from 60 to 400 g/liter or, preferably, from 80 to 400 g/liter.

The efficiency of culture of the fungus in the above defined conditions can further be improved when the liquid culture medium contains acetic acid or an acetate such as an alkali acetate and ammonium acetate at a concentration in the range from 0.1 to 20 g/liter.

When the fungal body has been obtained in the above described method, the lipid rich in the content of γ-linolenic acid can readily be prepared by extracting from the fungal body, optionally, after separation from the liquid culture medium, for example, using an organic solvent and γ-linolenic acid can be prepared by concentrating according to a known procedure.

DETAILED DESCRIPTION OF THE PREFERRED EMBODIMENTS

The above described inventive method has been completed on the basis of the discovery that, when cultured under specific culture conditions, filamentous fungus stocks of *Mortierella isabellina*, *M. vinacea*, *M. ramanniana*, *M. ramanniana* var. *angulispora* and *M. nana* can give fungal bodies of very high lipid content of 35 to 70% by weight with high productivity and that the lipid is rich in the content of γ-linolenic acid. The possibility of such a high-density culture of Mortierella fungi has been quite unexpected because it is generally accepted that filamentous fungi multiplying with hyphae can hardly be cultured in a high density condition of the fungal body, different from bacteria and yeast. The present discovery, however, shows that these specific fungi can multiply in small discrete units without extending the hyphae in a culture medium containing a carbohydrate as the carbon source under an agitating condition by aeration when the velocity of aeration is increased to give a possibility of obtaining a fungal body of high lipid content in very high density per unit volume of te medium. For example, glucose as the starting carbohydrate contained in the culture medium in a concentration as high as 270 g/liter is exhaustively consumed by the culture of the fungus at 30° C. for 72 hours to give 100 g/liter medium or more of the fungal body as dried containing about 50 g/liter of the lipid corresponding to a lipid content of about 50%.

As is understood from the above description, the scope of the inventive method for the preparation of a fungal body containing a large amount of lipids consists in the culture of a specific filamentous fungal stock under specific culture conditions. The fungal stocks used in the inventive method all belong to the genus of Mortierella and kept and available at the Institute of Fermentation, Osaka and also registered in the IFO Catalogue bearing the respective IFO numbers including *M. isabellina* (IFO 7824, 7873, 7884, 8183, 8308 and 8309), *M. vinacea* (IFO 6738), *M. ramanniana* (IFO 8287), *M. ramanniana* var. *angulispora* (IFO 6744 and 8187) and *M. nana* (IFO 8794).

In culturing the above named Mortierella fungi in a liquid culture medium, the medium should contain a carbohydrate as the carbon source which may be, for example, glucose, fructose, saccharose, molasses, starch, saccharification liquid of wood and others. The concentration of the carbohydrate in the culture medium should be high enough in the range from 60 to 400 g per liter or, preferably, from 80 to 400 g/liter of the medium. The nitrogen source to be added to the culture medium may be any one of inorganic nitrogen compounds such as ammonium nitrate, ammonium sulfate, ammonium chloride and ammonium phosphate and organic materials such as urea, peptone, yeast extract and corn steep liquor. The culture medium also should contain small amounts of inorganic metal salts such as potassium dihydrogenphosphate, dipotassium hydrogenphosphate, sodium chloride, iron (II) sulfate, magnesium sulfate, zinc sulfate and the like. It is of course optional that certain micronutrients and other nutritive substances may be added to the culture medium according to need.

The culturing of the above mentioned filamentous fungus is performed usually in a liquid medium with agitation by aeration. The value of pH of the culture medium should preferably be in the range from 4.0 to 6.0 and culturing is continued for 2 to 15 days at a temperature in the range from 15° to 40° C. under agitation at a relatively high velocity of 300 to 800 r.p.m. with aeration at a rate of 0.5 to 2 v.v.m. In this manner, a fungal body of very high lipid content is produced in the culture medium in a high density so that the body is separated from the culture medium and the lipid contained therein is extracted by a suitable means such as extraction by use of an organic solvent. It is noted that, in accordance with the culturing method of the present invention, the multiplication of the filamentous fungus takes place with relatively suppressed extension of the hyphae in extremely minute discrete units each containing only 1 to 10 cells so that the separation of the fungal body from the culture medium is greatly facilitated by use of, for example, a dehydrator or the like machine to give a body with an advantageously low water content of as low as about 60%. The recovery of the lipid from the thus dehydrated fungal body is undertaken according to a conventional procedure such as extraction with an organic solvent. The thus obtained lipid is rich in the content of γ-linolenic acid which can be separated in a concentrated form from the mixed fatty acids or mixed fatty acid esters by a known method such as the urea adduct process and cooling separation process.

It has been unexpectedly discovered that the culturing efficiency of the fungal stock or the content of γ-linolenic acid in the fungal body can further be improved by the addition of acetic acid or an alkali metal acetate such as sodium and potassium acetates to the culture medium. The preferable concentration of the acetic acid or acetate in the culture medium is in the range from 0.1 to 20 g/liter depending on the culturing conditions such as the concentration of the carbon source and others. In this case, the pH of the culture medium is preferably in the range from 3.0 to 6.0 and culturing is complete within 10 days. The advantage by the addition of acetic acid or acetate is of course obtained even when the concentration of the carbon source in the culture medium is relatively low such as 20 g/liter but is more remarkable when the concentration thereof is 60 g/liter or higher.

The inventive method performed in the above described manner can afford a possibility of the production of a lipid with very high productivity because the culturing of the filamentous fungus can be performed in very high densities to give a fungal body of very high lipid content by use of a culture medium containing a carbohydrate as the carbon source in a high concentration hitherto not used in the culture of filamentous fungi along with ease and high efficiency in the recovery of the lipid from the thus grown fungal body.

The advantage in the productivity is particularly apparent from the calculation of the capacity of the apparatus required for unit production of the lipid. For example, the hourly production of the fungal body per unit volume of the culture medium would be 1.7 g fungal body per liter per hour assuming a fungal body multiplication of 100 g/liter medium and in consideration of the culture time necessary to obtain this multiplication estimated from the results of the experimentation described below. Therefore, a constant yearly running of 1000 $m^3$ of the culture medium, which is in practice possible by a combined cycling use of 3 culture tanks each having a capacity of 800 $m^3$, would provide a yearly fungal body production of 14,000 tons/year corresponding to a yearly lipid production of 7,000 tons/year assuming a 50% content of the lipid in the body.

In addition, the lipid produced in this manner contains more than 95% of fats or oils, i.e. triglycerides, so that it is useful not only as a food but also as a starting material for the manufacture of various products derived from fats and oils. The phospholipids and glycolipids contained in the lipid are useful as an ingredient of medicines or as a surface active agent. Furthermore, the fungal body residue after extraction of the lipid is composed mainly of proteins and nucleic acids respectively useful in the applications as a provender and medicines.

Thus, the present invention provides an industrial possibility of microbiologically producing a lipid containing a large amount of unsaturated fatty acids or, in particular, $\gamma$-linolenic acid with high productivity. The inventive method is highly useful as a method for the preparation of a $\gamma$-linolenic acid-containing lipid or as a method for the modification of a lipid. Particular advantages are obtained in the preparation of a $\gamma$-linolenic acid-containing lipid in substitution for the conventional methods starting with extraction from the seeds of specific plants.

The following examples illustrate the inventive method in more detail but do not limit the scope of the invention in any way.

EXAMPLE 1

Culture media were prepared each by dissolving in 1000 ml of deionized water a varied amount of a carbon source which was either glucose or molasses, 2 g of potassium dihydrogenphosphate $KH_2PO_4$, 0.3 g of magnesium sulfate $MgSO_4.7H_2O$, 0.1 g of sodium chloride NaCl, 0.2 g of malt extract, 0.2 g of yeast extract, 0.1 g of peptone, 10 mg of iron (II) sulfate $FeSO_4.7H_2O$, 10 mg of calcium chloride $CaCl_2.2H_2O$, 0.2 mg of copper (II) sulfate $CuSO_4.5H_2O$, 1.0 mg of manganese sulfate $MnSO_4.4H_2O$, each per 60 g of the carbon source, and a varied amount of a nitrogen source which was either ammonium sulfate or urea. The formulation of the carbon source and the nitrogen source is shown in Table 1 below. When 60 g of glucose and 3 g of ammonium sulfate were added to the medium as the carbon source and the nitrogen source, respectively, the C/N ratio, i.e. the weight ratio of the carbon atoms to nitrogen atoms, in the culture medium was about 40 although the C/N ratio was varied in some tests to examine the effects of the nitrogen concentration or C/N ratio.

Into a culture tank of 10 liters or 30 liters capacity were introduced 6 liters or 20 liters, respectively, of the above prepared culture medium to which either one of the above named fungal stocks was inoculated and cultured therein at 30° C. or 35° C. under agitation at a velocity of 300 to 700 r.p.m. with aeration at a rate of 0.5 to 2.0 v v.m. In the course of culturing in this manner, a 100 ml portion of the culture medium was periodically taken out of the tank and filtered to separate the fungal body from the culture medium. A part of the thus collected body was subjected to the determination of the water content by drying in a thermostat at 120° C. for 24 hours after exact weighing and the remainder was used for the extraction of the lipid. Thus, the wet fungal body obtained by filtration was added to a 2:1 by volume mixture of chloroform and methyl alcohol and homogenized in the presence of glass beads to effect simultaneous grinding of the body and extraction of the lipid from the ground body into the solvent. This extraction procedure was repeated 5 times each with a fresh portion of the solvent and all the extract solutions were combined together. After purification by the method of partition washing according to Folch, the solvents were removed from the combined extract solution by evaporation under reduced pressure and the amount of the total lipid was determined by weighing the residual matter.

The culture medium after separation of the fungal body by filtration was subjected to high-performance liquid chromatography (HPLC) to determine the concentration of the unconsumed carbohydrate, i.e. glucose per se or glucose, fructose and saccharose in the molasses. When the results of this high-performance liquid chromatography indicated complete consumption of the carbohydrate in the culture medium, the culturing was terminated and the time from the start was recorded as shown in Table 1.

A portion of the lipid extracted from the fungal body was converted to the methyl ester and subjected to gas chromatography to determine the relative composition of the individual fatty acids. The remainder portion of the lipid was separated column-chromatographically into neutral and polar lipids using Unisil as the adsorbent and chloroform and methyl alcohol as the eluants and the amount of each lipid was determined. Each of the lipids was also converted to the methyl ester and subjected to the gas chromatography for the determination of the relative composition of the fatty acids.

Table 2 below summarizes the results of the Cultures No. 1 to No. 14 under the conditions shown in Table 1 including the yield of the fungal body DC in g on the dry basis per liter volume of the culture medium, the yield of the total lipid TL in g per liter volume of the culture medium, the content of the total lipid in the fungal body TL/DC in %, the content of the neutral lipid NL in the fungal body NL/DC in %, the content of the polar lipid PL in the fungal body PL/DC in %, the contents of γ-linolenic acid in the total lipid, neutral lipid and polar lipid in %, the overall content of γ-linolenic acid in the fungal body in % and the yield of γ-linolenic acid in g per liter volume of the culture medium.

As is understood from Tables 1 and 2, the multiplication of the fungus was very rapid even in an unconventionally high concentration of the carbon source of 100 g/liter or more or, in some cultures, 200 g/liter or more to give a yield of the fungal body of 40 to 156 g/liter on the dry basis containing 32 to 58% by weight of the lipid corresponding to a yield of the lipid of 13 to 83 g/liter. The content of γ-linolenic acid in the fatty acids of the thus obtained lipid was as high as 3.3 to 11.0% by weight to be comparable with the content in the plant seeds conventionally used as the starting material of γ-linolenic acid preparation. Further, the content of γ-linolenic acid is particularly high in the polar lipid reaching 20% by weight or higher in some cases. The content of γ-linolenic acid in the fungal body was 1.3 to 4.1% by weight on the dry basis, which value is also comparable with that in the plant seeds, corresponding to a yield of γ-linolenic acid of 0.9 to 3.4 g per liter volume of the culture medium.

EXAMPLE 2

According to the procedure for the extraction of lipids from fungal body described in Example 1, 100 g of lipid were prepared from 900 g of the wet fungal body obtained in Culture No. 13 in Example 1 corresponding to 270 g of dry fungal body. Esterification of the lipid according to the conventional procedure gave 92 g of a methyl ester mixture of the fatty acids, of which gas chromatographic analysis was undertaken for the relative fatty acid composition to give a result that the mixture was composed of 31.3% of palmitic acid, 1.4% of palmitooleic acid, 5.6% of stearic acid, 44.7% of oleic acid, 9.2% of linoleic acid and 6.4% of γ-linolenic acid. This mixture of the fatty acid methyl esters was subjected to the urea adduct process repeated three times according to the conventional procedure to give 7.2 g of a fatty acid mixture in which the γ-linolenic acid had been concentrated to a concentration of 48.2% accompanied by 45.9% of linoleic acid, 4.1% of oleic acid and 1.8% of other fatty acids.

EXAMPLE 3

A culture medium was prepared by dissolving 30 g of glucose, 2 g of potassium dihydrogenphosphate $KH_2PO_4$, 0.3 g of magnesium sulfate $MgSO_4.7H_2O$, 0.1 g of sodium chloride NaCl, 10 mg of iron (II) sulfate $FeSO_4.7H_2O$, 10 mg of calcium chloride $CaCl_2.2H_2O$, 0.2 mg of copper sulfate $CuSO_4.5H_2O$, 1.0 mg of zinc sulfate $ZnSO_4.7H_2O$, 1.0 mg of manganese chloride $MnCl_2.4H_2O$, 2 mg of thiamine hydrochloride, 0.02 mg of D-biotin and 3 g of ammonium sulfate, the C/N ratio in the medium being 22.2, in 1000 ml of deionized water, of which the value of pH was adjusted to 4.6, with or without further admixture of 1 g of acetic acid or 5 g of sodium or potassium acetate.

A 400 ml portion of the thus prepared culture medium taken in an Erlenmeyer flask of 1000 ml capacity was inoculated with one of the Mortierella fungi named before and culture of the fungus was performed by shaking the flask at a velocity of 150 r.p.m. for 7 days at a culture temperature of 30° C. After completion of the culture in this manner, the fungal body in the medium was collected by filtration or centrifugal separation. A portion of the collected fungal body was used for the determination of the water content therein by exactly weighing before and after drying by heating for 24 hours in an air oven at 120° C. The remainder portion of the wet fungal body was subjected to the extraction of the lipid in the same manner as in Example 1. The thus extracted lipid was converted to the methyl ester according to the conventional procedure and the mixture of the methyl esters was analyzed by gas chromatography to determine the relative fatty acid composition.

Table 3 below gives the results of the culture tests making comparison between the cultures with or without addition of the acetic acid or acetate along with the yields of the fungal body and lipid each in g per liter of the medium, content of the lipid in % in the fungal body, fungal body coefficient, i.e. yield of the fungal body in g per 100 g of glucose consumption, lipid coefficient, i.e. yield of the lipid in g per 100 g of glucose consumption, content of γ-linolenic acid in % in the overall fatty acids, content of unsaturated fatty acids in % in the overall fatty acids and unsaturation factor, i.e. the average number of unsaturated linkages per molecule of the overall fatty acids.

As is understood from the results shown in Table 3, the addition of acetic acid or acetate to the culture medium always had an effect to increase the yield of the fungal body for the same species of fungus reaching twice or more in most of the species in comparison with the culture without addition thereof. This advantageous effect was even more remarkable when comparison was made for the yield of the lipid increasing to 1.5 to 6 times by the addition of acetic acid or acetate. The content of the lipid in the fungal body was increased by 10 to 20% by the addition of acetic acid or acetate though less significant in some cases. Accordingly, the fungal body coefficient and lipid coefficient, i.e. the yields of the fungal body and lipid in g per 100 g consumption of glucose, respectively, were greatly increased by the addition of acetic acid or acetate.

In connection with the composition of the fatty acids in the lipid, the content of γ-linolenic acid was always increased by the addition of acetic acid or acetate and an increase of 1.7 to 20.1% was noted in the content of the unsaturated fatty acids. As was evidenced by the significant increase in the unsaturation factor, the addition of acetic acid or acetate had an effect of not only increasing the overall yield of the unsaturated fatty acids but also increasing the degree of unsaturation, i.e. average number of unsaturated linkages per molecule, in the unsaturated fatty acids. Thus, the results of this example evidence that the nature of the lipid can be improved or modified in such a way that the yield of the unsaturated fatty acids including γ-linolenic acid as a highly unsaturated fatty acid is increased by the addition of acetic acid or acetate to the culture medium.

EXAMPLE 4

Liquid culture media were prepared in the same formulation as in Example 1 except that the concentration of glucose as the carbon source was varied from 85 to 200 g/liter, the concentration of each of the other ingredients being proportional to the concentration of glucose, and the nitrogen source in each medium was a combination of urea and ammonium sulfate each in a concentration indicated in Table 4 below to give a C/N ratio of about 60. In Table 4, Cultures No. 35 and No. 44 are for comparative purpose to show the effect of the addition of acetic acid or acetate. The pre-culture medium in each of the cultures No. 2 to No. 5 contained no acetate and Cultures No. 4 and No. 5 were performed by adding sodium acetate only at a moment 30 hours from the start of culture. Cultures No. 6 to No. 9, No. 11 and No. 12 were performed by adding sodium acetate already in the pre-culture medium in a concentration of 5 g/liter.

Culture of *Mortierella ramanniana* var. *angulispora* IFO 8187 was performed using the above prepared culture media in the same manner as in Example 1 except that a varied amount of sodium acetate indicated in Table 4 was further added to the culture medium to examine the effect of acetate addition. Cultures No. 35 to No. 43 were performed each in a culture tank of 10 liter capacity and Cultures No. 44 to No. 46 were performed each in a culture tank of 30 liter capacity.

The results of these culture tests are shown in Table 4 including the concentrations of glucose, urea, ammonium sulfate and sodium acetate, culture time in hours, yields of the fungal body and lipid each in g per liter of the culture medium, content of lipid in the fungal body in %, fungal body coefficient and lipid coefficient.

As is understood from the results shown in Table 4, in particular, for the cultures in the 10 liter culture tank, the addition of sodium acetate was always effective in increasing the yield of the lipid and the content of lipid in the fungal body. The yield of the fungal body was also increased in general by the addition of sodium acetate though not conclusive due to some anomalous results. In the culture tests using the 30 liter culture tank in which the concentration of glucose was equal or close to 200 g/liter, the addition of sodium acetate had an effect to slightly decrease the yield of the fungal body while significant improvement was obtained in the content of the lipid in the fungal body by 10% or more corresponding to an increase in the yield of the lipid by 20% or more and accordingly to a remarkable improvement in the lipid coefficient indicating that the effect of sodium acetate is not critically dependent on the concentration thereof at least in the range from 0.3 to 5 g/liter.

TABLE 1

| Culture No. | IFO No. of fungus | Capacity of culture tank, liters | Carbon source[1], g/liter | Nitrogen source[2], g/liter | Culture temperature, °C. | Culture time, hours |
|---|---|---|---|---|---|---|
| 1 | 7884 | 30 | 390 | 17 | 30 | 168 |
| 2 | 7884 | 30 | 270 | 10 | 30 | 72 |
| 3 | 7884 | 30 | 280 | 10 | 30 | 108 |
| 4 | 7884 | 10 | 220 | 5.7 | 30 | 72 |
| 5 | 7824 | 10 | 200 | 6.5 | 30 | 72 |
| 6 | 8183 | 30 | 165 | 4.0 | 30 | 72 |
| 7 | 8308 | 10 | 200 | 6.5 | 30 | 72 |
| 8 | 8309 | 10 | 140 | 3.5 | 30 | 57 |
| 9 | 6738 | 30 | 200 | 6.5 | 30 | 72 |
| 10 | 8794 | 10 | 200 | 6.5 | 30 | 96 |
| 11 | 8287 | 10 | 200 | 6.5 | 30 | 96 |
| 12 | 6744 | 10 | 100 | 3.0 | 30 | 56 |
| 13 | 8187 | 30 | 190 | 6.5 | 30 | 66 |
| 14 | 8187 | 30 | 140 | 4.0 | 35 | 96 |

[1]The carbon source was glucose in all cultures excepting Culture No. 3 in which molasses was used instead.
[2]The nitrogen source was urea in all cultures excepting Culture No. 12 in which ammonium sulfate was used instead.

TABLE 2

| Culture No. | Yield of DC, g/liter | Yield of TL, g/liter | TL/DC, % | NL/DC, % | PL/DC, % | γ-Linolenic acid in TL, % | in NL, % | in PL, % | in DC, % | yield, g/liter |
|---|---|---|---|---|---|---|---|---|---|---|
| 1 | 156.4 | 83.1 | 53.1 | — | — | 4.5 | — | — | 4.1 | 3.4 |
| 2 | 103.5 | 49.4 | 47.7 | — | — | 4.4 | — | — | 1.9 | 2.0 |
| 3 | 104.2 | 53.1 | 51.0 | — | — | 3.9 | — | — | 1.8 | 1.9 |
| 4 | 77.2 | 44.1 | 57.1 | 53.6 | 3.5 | 4.1 | 3.8 | 15.5 | 2.1 | 1.6 |
| 5 | 76.3 | 34.9 | 45.8 | 43.6 | 2.2 | 6.6 | 6.2 | 21.2 | 2.8 | 2.1 |
| 6 | 69.4 | 24.1 | 34.7 | 33.6 | 1.1 | 4.2 | 3.9 | 16.5 | 1.3 | 0.9 |
| 7 | 73.2 | 35.4 | 48.3 | 46.4 | 1.9 | 3.5 | 3.3 | 15.6 | 1.5 | 1.1 |
| 8 | 43.2 | 15.9 | 36.7 | 33.9 | 1.8 | 10.0 | 9.4 | 14.5 | 3.2 | 1.4 |
| 9 | 79.7 | 29.6 | 37.1 | 34.0 | 3.1 | 7.8 | 7.5 | 19.1 | 2.6 | 2.1 |
| 10 | 72.5 | 33.1 | 45.6 | 43.5 | 2.1 | 7.5 | 7.3 | 12.1 | 3.0 | 2.2 |
| 11 | 69.8 | 27.6 | 39.5 | 38.0 | 1.5 | 5.8 | 5.4 | 11.8 | 2.0 | 1.4 |
| 12 | 40.4 | 12.8 | 31.8 | 29.4 | 2.4 | 11.2 | 11.0 | 23.7 | 3.2 | 1.2 |
| 13 | 77.6 | 29.3 | 37.8 | 35.2 | 2.6 | 6.4 | 6.2 | 23.6 | 2.2 | 1.7 |
| 14 | 52.2 | 20.2 | 38.8 | — | — | 9.7 | — | — | 3.4 | 1.8 |

(*) See text for the meaning of DC, TL, NL and PL.

TABLE 3

| Culture No. | IFO No. of fungus | Additive[1] | Yield of fungal body, g/liter | Yield of lipid, g/liter | Content of lipid, % | Fungal body coefficient[2] | Lipid coefficient[3] | γ-Linolenic acid, % | Overall unsaturated fatty acids, % | Unsaturation factor |
|---|---|---|---|---|---|---|---|---|---|---|
| 15 | 7824 | — | 4.35 | 2.01 | 45.8 | 14.6 | 6.7 | 8.0 | 71.4 | 1.03 |
| 16 | | NaOAc | 8.83 | 4.38 | 49.6 | 29.5 | 14.6 | 10.7 | 75.1 | 1.07 |
| 17 | 7873 | — | 5.54 | 2.19 | 40.2 | 18.2 | 7.3 | 4.7 | 63.5 | 0.84 |
| 18 | | NaOAc | 9.95 | 5.72 | 57.5 | 33.2 | 19.1 | 6.7 | 65.0 | 1.10 |
| 19 | 7884 | — | 5.55 | 2.21 | 39.9 | 18.5 | 7.4 | 3.9 | 59.0 | 0.75 |
| 20 | | NaOAc | 7.08 | 4.04 | 56.9 | 23.6 | 13.5 | 4.2 | 67.9 | 0.88 |
| 21 | | KOAc | 6.30 | 3.84 | 61.3 | 21.0 | 12.8 | 4.2 | 69.8 | 0.89 |
| 22 | | AcOH | 7.30 | 3.15 | 42.8 | 21.9 | 10.5 | 4.0 | 64.3 | 0.85 |
| 23 | 8183 | — | 9.08 | 3.37 | 37.2 | 30.3 | 11.2 | 4.2 | 64.6 | 0.82 |
| 24 | | NaOAc | 9.98 | 4.65 | 46.6 | 33.2 | 15.5 | 7.9 | 73.7 | 1.00 |
| 25 | 8309 | — | 5.25 | 1.30 | 24.7 | 17.5 | 4.3 | 5.6 | 68.4 | 0.93 |
| 26 | | NaOAc | 10.90 | 6.03 | 55.3 | 36.3 | 20.1 | 10.0 | 88.5 | 1.36 |

TABLE 3-continued

| Culture No. | IFO No. of fungus | Additive[1] | Yield of fungal body, g/liter | Yield of lipid, g/liter | Content of lipid, % | Fungal body coefficient[2] | Lipid coefficient[3] | γ-Linolenic acid, % | Overall unsaturated fatty acids, % | Unsaturation factor |
|---|---|---|---|---|---|---|---|---|---|---|
| 27 | 6738 | — | 5.03 | 1.85 | 36.8 | 16.8 | 6.2 | 3.2 | 56.3 | 0.67 |
| 28 |  | NaOAc | 10.10 | 5.19 | 51.4 | 33.7 | 17.3 | 3.6 | 64.5 | 0.83 |
| 29 | 8794 | — | 4.52 | 2.33 | 51.3 | 15.1 | 7.8 | 5.3 | 58.1 | 0.78 |
| 30 |  | NaOAc | 9.15 | 4.42 | 48.3 | 30.5 | 14.8 | 6.1 | 71.9 | 0.95 |
| 31 | 8287 | — | 3.65 | 1.49 | 40.9 | 12.2 | 5.0 | 5.8 | 64.6 | 0.81 |
| 32 |  | NaOAc | 5.20 | 2.75 | 52.9 | 17.3 | 9.2 | 7.4 | 68.0 | 0.96 |
| 33 | 8187 | — | 3.80 | 0.71 | 18.8 | 12.7 | 2.4 | 9.1 | 61.7 | 0.82 |
| 34 |  | NaOAc | 8.33 | 4.31 | 51.8 | 27.7 | 14.4 | 9.2 | 77.8 | 1.00 |

[1]AcOH: acetic acid; NaOAc: sodium acetate; KOAc: potassium acetate
[2]Yield of fungal body in g per 100 g of glucose consumption
[3]Yield of lipid in g per 100 g consumption of glucose

TABLE 4

| Culture No. | Glucose, g/liter | Urea, g/liter | Ammonium sulfate, g/liter | Sodium acetate, g/liter | Culture time, hours | Yield of fungal body, g/liter | Yield of lipid, g/liter | Content of lipid, % | Fungal body coefficient | Lipid coefficient |
|---|---|---|---|---|---|---|---|---|---|---|
| 35 | 90 | 1.3 | 1.5 | — | 48 | 31.9 | 11.9 | 37.2 | 35.4 | 13.2 |
| 36 | 90 | 1.3 | 1.5 | 5 | 51 | 34.0 | 17.2 | 50.7 | 37.8 | 19.1 |
| 37 | 90 | 1.3 | 1.5 | 10 | 69 | 36.1 | 18.4 | 51.0 | 40.1 | 20.5 |
| 38 | 90 | 1.3 | 1.5 | 5 | 63 | 40.5 | 17.0 | 41.9 | 45.0 | 18.9 |
| 39 | 90 | 1.3 | 1.5 | 10 | 69.5 | 36.8 | 17.9 | 48.5 | 40.9 | 19.8 |
| 40 | 85 | 1.33 | 1.5 | 5 | 45 | 31.3 | 14.5 | 46.4 | 36.8 | 17.1 |
| 41 | 85 | 1.33 | 1.5 | 10 | 51 | 29.3 | 15.7 | 53.4 | 34.5 | 18.4 |
| 42 | 85 | 1.33 | 1.5 | 2.3 | 46 | 32.7 | 14.7 | 45.0 | 38.4 | 17.3 |
| 43 | 85 | 1.33 | 1.5 | 0.3 | 50 | 34.4 | 15.2 | 44.2 | 40.7 | 17.9 |
| 44 | 190 | 5 | 2.55 | — | 66 | 77.6 | 28.8 | 37.1 | 40.9 | 15.2 |
| 45 | 185 | 5 | 2.55 | 5 | 98 | 66.8 | 33.8 | 50.6 | 36.1 | 18.2 |
| 46 | 200 | 5 | 2.55 | 0.3 | 79 | 74.5 | 35.9 | 48.2 | 37.3 | 18.0 |

What is claimed is:

1. A method which comprises the steps of:
   (a) culturing with agitation under aerobic conmditions a fungus of the species Mortierella selected from the group consisting of M. isabellina IFO 7824, 7873, 7884, 8183, 8308 or 8309; M. vinacea IFO 6738; M. ramanniana IFO 8287; M. ramanniana var agulispora IFO 6744 or 8187 and M. nana IFO 8794 at a pH of from 4 to 6 in an aqueous liquid culture medium containing carbohydrate as the carbon source in a concentration from 100 to 400 g/liter, and additionally containing acetic acid or an alkali acetate in a concentration of from 0.1 to 20 g/liter to grow a fungal body containing from 35% to 70% lipid on a total dry weight basis having a γ-linolenic acid content of from 3% to 11%; and (b) extracting the lipid from the fungal body.

2. The method as claimed in claim 1 wherein the carbohydrate is glucose or molasses.

3. The method as claimed in claim 1 wherein the alkali acetate is sodium acetate or potassium acetate.

4. The method as claimed in claim 1 wherein the pH value of the liquid culture medium is in the range from 4.0 to 6.0.

5. The method as claimed in claim 1 wherein the pH value of the liquid culture medium is in the range from 3.0 to 6.0.

* * * * *